United States Patent [19]
Drewes et al.

[11] 4,349,898
[45] Sep. 14, 1982

[54] SONIC WEAPON SYSTEM

[75] Inventors: William Drewes, 100 Ellison Ave., Bronxville, N.Y. 10708; Edward M. Vlicki, Elmwood Park, N.J.

[73] Assignee: William Drewes, Bronxville, N.Y.

[21] Appl. No.: 959,302

[22] Filed: Nov. 9, 1978

[51] Int. Cl.$^3$ .................................................. H04B 1/02
[52] U.S. Cl. ...................................... 367/138; 367/92; 367/139
[58] Field of Search ............... 367/92, 137, 138, 139

[56] References Cited

U.S. PATENT DOCUMENTS 3,612,211 10/1971 Clark .............................. 367/139 X
3,613,069 10/1971 Cary, Jr. et al. ...................... 367/92

OTHER PUBLICATIONS

Rudenko et al., "TheoreticalFoundations of Nonlinear Acoustics", (English Translation) Consultant's Bureau, New York, 1977, pp. 145–147.

Primary Examiner—Richard A. Farley
Attorney, Agent, or Firm—Hubbell, Cohen, Stiefel & Gross

[57] ABSTRACT

A system for transmitting a parametrically pumped sonic signal through a transmission medium to a remote location is disclosed. The preferred system, which is particularly intended for use as a sonic weapon, comprises a sound source; means for separating the sound into a plurality of discrete frequency components including a fundamental component and at least one additional component, each additional component having a frequency twice that of the next lowest frequency component; means for adjusting the phase difference between each frequency component and the next lowest frequency component to substantially 90°; means for colinearly focusing the components on the remote location; and means for rendering the transmission medium nonlinear between the focusing means and the remote location.

36 Claims, 11 Drawing Figures

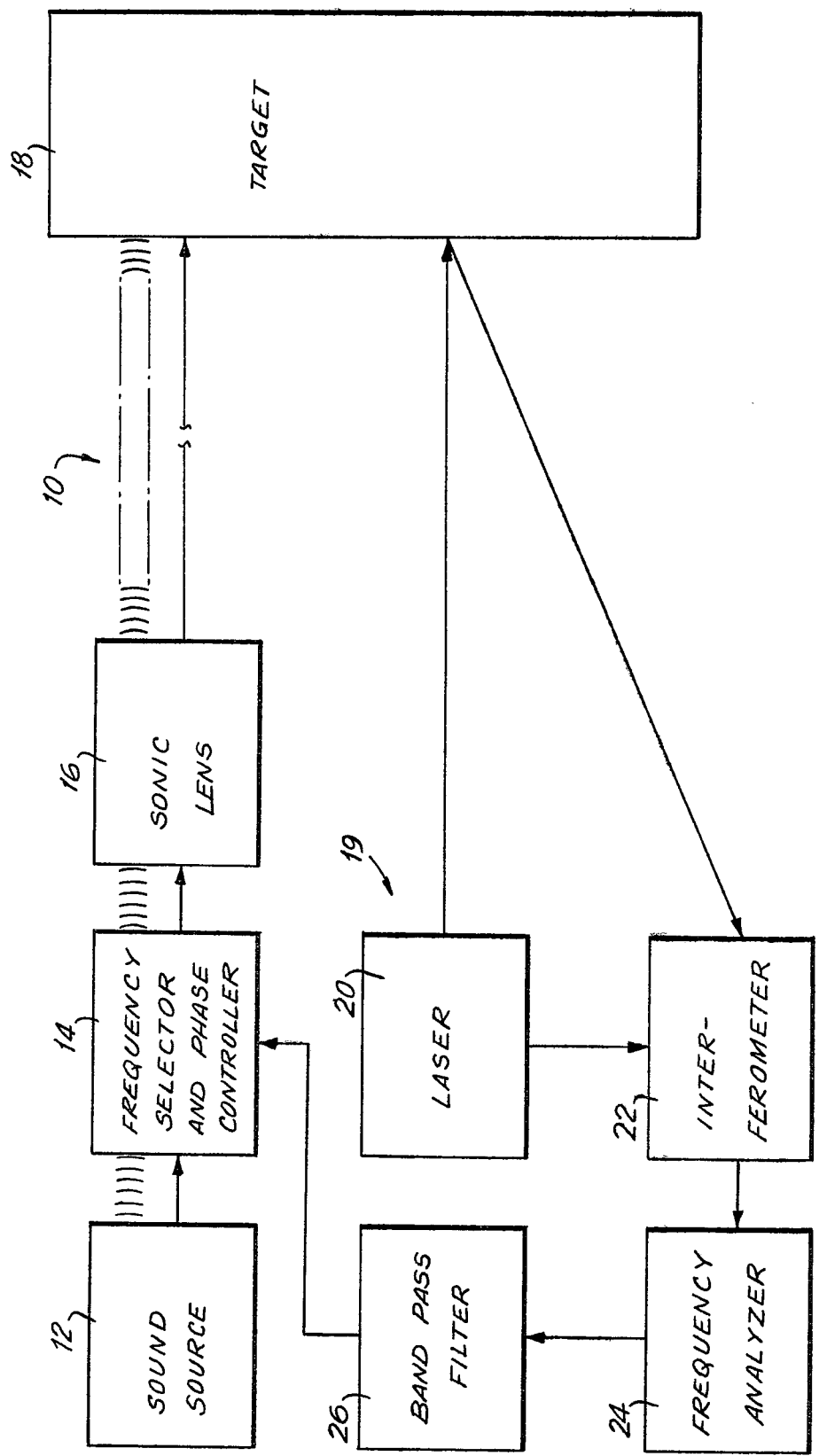

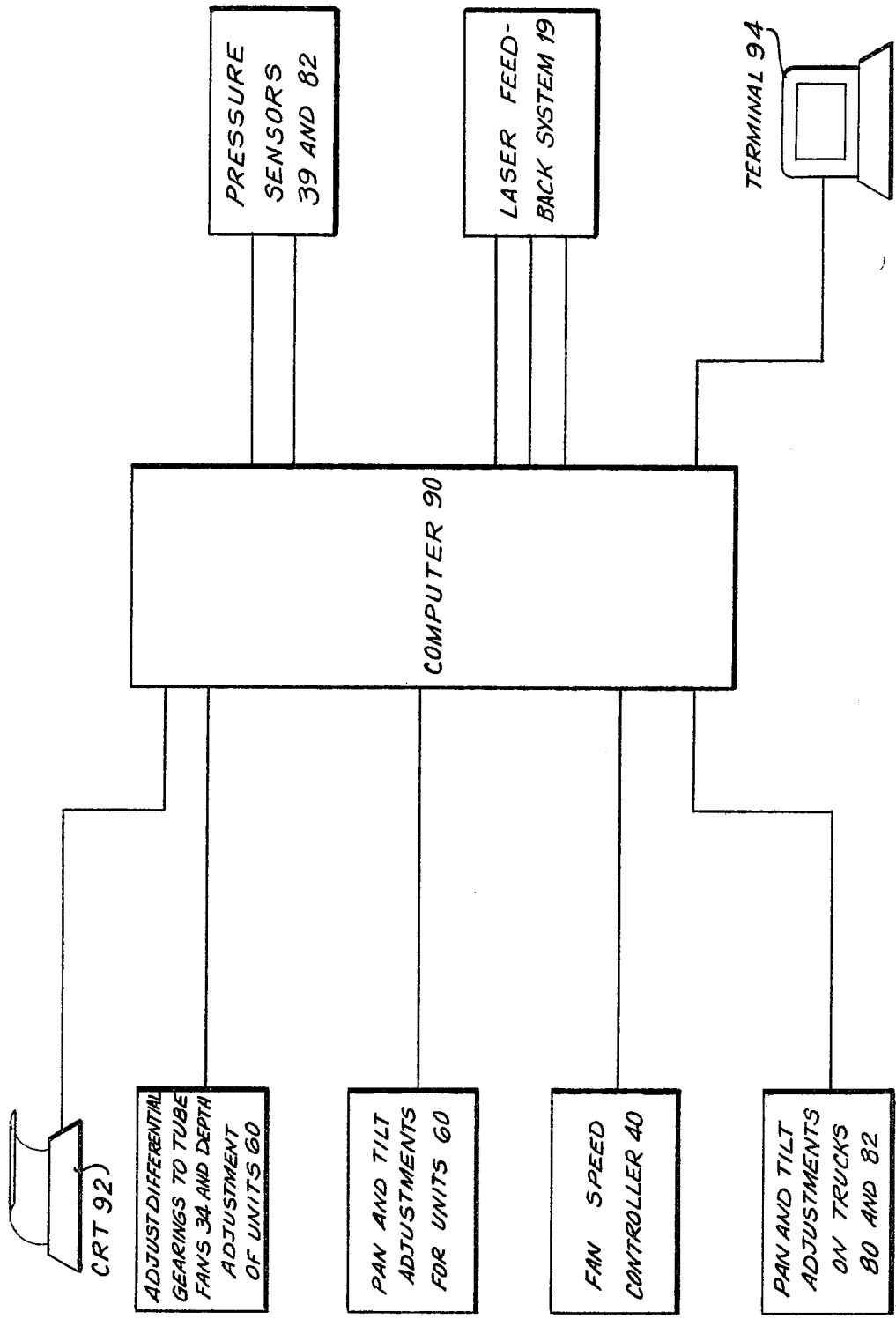

SONIC WEAPON SYSTEM

BACKGROUND OF THE INVENTION

1. Field of the Invention

This invention pertains to sonic transmission systems and more particularly to systems for transmitting low frequency sonic signals with long range characteristics. Most particularly, this invention pertains to a parametrically pumped sonic weapon system.

2. Statement of the Prior Art

In order to destroy a target or kill or injure enemy personnel using a sonic signal, it is necessary to vibrate the target at or near its resonant frequency. Since the resonant frequency of commonly encountered structural targets is relatively low, typically 5–20 hertz, a low frequency sonic beam is required. In addition, the sonic beam must have sufficient range to be effective as a weapon. While these two criteria are simple to state, they are not easy to implement. The reason is Rayleigh's Law which may be written in equation form as follows:

$$\delta = 1.22 \; \lambda/\sin\phi$$

where $\delta$ equals the radius of the central disc of energy, $\lambda$ equals the wavelength of the focused beam and $\phi$ equals the angle subtended by the lens at the focal distance. For example, Rayleigh's Law predicts that the lens diameter required to focus a 10 hertz wave to within a 50 foot diameter zone of focus at a range of one mile is about 26,484 feet or about five miles.

Until recently, Rayleigh's Law was thought to be an absolute bar to the long-range propogation of a low frequency wave. Recently, however, it has been recognized that if two colinear sound beams are introduced into a nonlinear transmission medium, the interaction between them results in the production of the difference frequency. Thus, if the frequency of one of the beams is f and the frequency of the other beam is 2f, then the difference frequency component will also be f and may be used to augment the lower frequency sound beam. Moreover, the difference frequency component will have the range characteristics of the higher frequency component. However, this augmentation, commonly referred to as parametric pumping, will only take place if the phase difference between the two signals at the starting point of the interaction is approximately 90°. Otherwise, the component produced by the non-linear interaction will tend to oppose the lower frequency signal. The theoretical basis for these conclusions is set forth in an article by O. V. Rudenko and S. I. Soluyan entitled Theoretical Foundations of Nonlinear Acoustics (English translation) Consultant's Bureau, New York 1977, pp. 145–157. Applicant is not aware of any system which utilizes these principles to focus low frequency sonic signals over relatively large distances much less one that does so with sufficient power to destroy remote targets or kill or injure enemy personnel.

SUMMARY OF THE INVENTION

According to the present invention, I have developed a sonic weapon system which takes advantage of the interaction between colinear beams in a nonlinear medium to transmit low frequency sonic signals to remote targets, structural or human, with sufficient power to destroy them. The basic system includes a high level sonic source, means for separating the raw output from the sonic source into discrete frequency components, means for adjusting the phasing between these components and means for focusing them on the target.

The sonic source may comprise any sound source having a sufficient power output capacity to maintain destructive levels at the target and render the transmission medium, typically air, nonlinear. Commercially available jet and nuclear engines are sufficient for this purpose and their use is presently preferred.

Although nonlinear augmentation as between a fundamental signal frequency f and a pump signal frequency 2 f is known, it is desirable for weapon systems applications to provide still further augmentation. This may be effected by adding a second pump signal having a frequency (4 f) twice that of the first pump signal (2 f), a third pump signal (8 f) having a frequency twice that of the second pump signal (4 f), and so on. For the same reason and with the same effect that the 2 f pump signal augments the fundamental signal, the 4 f pump signal will augment the 2 f pump signal which, in turn, augments the fundamental signal. Similarly, the 8 f pump signal will augment the 4 f pump signal which augments the 2 f pump signal, and so on. As is the case between the 2 f pump signal and the fundamental signal, each successive pump signal must be 90° out of phase with the signal it augments.

The result is a low frequency sonic wave having the range characteristics of the highest frequency pump signal. The frequency of the highest frequency pump signal is, in turn, only limited by the expected losses due to divergence, sound absorption, transfer of energy to higher harmonics, etc. Based on these considerations, a maximum pump frequency of about 5,000 Hertz is presently preferred.

The frequency selector and phase controller serves to separate the raw output from the sonic source into the required fundamental and pump signal frequencies. The frequency selector and phase controller preferably comprises a combination of tubes, fans and masks. The input ends of the tubes are positioned to receive the raw output from the source such that the source output is distributed substantially equally among the tubes. A fan and a mask are disposed in the output end of each of the tubes, the mask being fixed relative to the tube.

The fan and mask in each tube are dimensioned such that as the fan rotates, it will alternately pass and block the flow of air through its corresponding tube. For example, a semicircular mask having a diameter equal to the internal diameter of the tube and a fan having a single matching semicircular blade are preferably used to generate the lower frequency components. Thus, as the blade rotates it will alternately pass through a position in which it is fully overlapped by the mask thus leaving half the output opening exposed, and a second position in which no portion of the blade is overlapped by the mask and the tube opening is fully blocked. This results in the generation of air pulses, the frequency of the pulses being dependent on the frequency of rotation of the fan blade. Since practical design limitations limit the maximum fan rotation speed, semicircular blades and masks will preferably not be used to generate the higher frequency components. According to the invention, this is overcome by adding additional mask sections and fan blades whereby each rotation of the fan blade results in the production of two or more pulses.

All the fans are preferably driven from a single rotating member through suitable gearing arrangements. The advantage of using a single rotating member, referred to herein as the fan speed controller, is that the fundamental and pump signal frequencies may be varied in step by simply varying the rotation rate of the controller.

Phasing is preferably accomplished by introducing a differential into the gearing for each fan. The differential permits each fan to be advanced or retarded relative to the others and thus may be used to control the relative timing and hence phase of the air pulses emanating from individual tubes.

The preferred sonic lens comprises a concave honeycomb array, each unit of the array comprising a hexagonal tubular structure closed at one end. By preselecting the cross-sections and lengths of the individual units, each unit may be tuned to enhance the reflection of a particular sonic frequency. Preferably, the array will have a number of honeycomb units tuned to each of the frequency components emanating from the frequency selector. Means are also preferably included for adjusting the pan and tilt of the individual honeycomb units whereby individual focusing of the honeycomb units may be effected. Also preferably included are means for adjusting the depth of each honeycomb unit relative to the others for fine tuning the phasing of the reflected signals.

The system is operated by focusing the output from the frequency selector and phase controller on the sonic lens and then focusing the sonic lens on the target. Upon activation of the source, the frequency selector will separate the raw output into discrete frequency components comprising a fundamental frequency at or near the resonant frequency of the target and successively higher pump frequencies. These components in turn strike the lens which then focuses them on the target. By selecting a sonic source with sufficient output to render the transmission medium nonlinear, the pump signals will augment the fundamental signal during transmission with the result being a high energy, low frequency sonic signal at the point of impact.

The destructive capability of the system during firing is maximized by adjusting the fan speed controller to match the fundamental frequency of the frequency selector and phase controller with the resonant frequency of the target. For this purpose, the preferred system also includes a laser interferometer for measuring the vibration frequency of the target. After appropriate signal conditioning, the information from the interferometer may be used to regulate the fan speed controller as required. Since accurate phasing is essential to effective operation, phasing is also preferably monitored during firing and adjusted as required. For example, signals from pressure sensors positioned to sense the amplitude peaks of each frequency component may be compared and this information used to implement phase control.

In one embodiment of the invention, level control of the individual frequency components is introduced by regulating the size of the opening to the individual tubes of the frequency selector. Portability may also be introduced as by using two flat bed trucks, one for the sound source and frequency selector and the other for the sonic lens and laser feedback system. The preferred embodiment also includes a computer for adjusting the various system parameters as required.

These as well as further features of the sonic weapon system according to the present invention will become more fully apparent from the following detailed description and annexed drawings of the preferred embodiment and suggested modifications thereof.

BRIEF DESCRIPTION OF THE DRAWINGS

In the drawings:

FIG. 1 is a diagrammatic illustration of the preferred parametrically pumped sonic weapon system according to the present invention;

FIG. 7 is a diagrammatic illustration of a computer system for regulating the operation of the preferred sonic weapon system;

DETAILED DESCRIPTION OF THE PREFERRED EMBODIMENTS

Figure 2A:
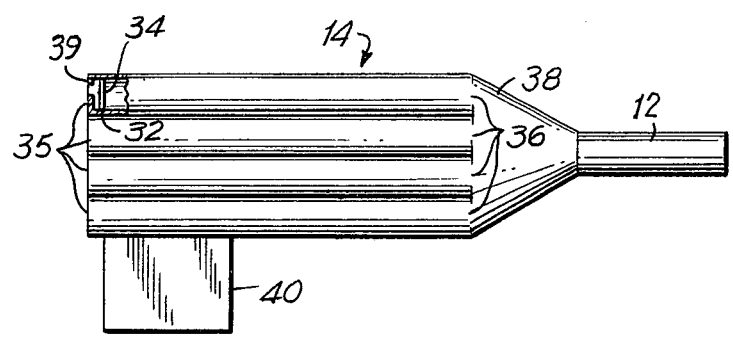
FIG. 2A is a partially diagrammatic side elevation of the preferred frequency selector and phase controller.

Referring now to the drawings, FIG. 1 is a diagrammatic illustration of the preferred sonic weapon system 10 in accordance with the present invention. As shown, the system 10 includes a high intensity sound source 12, a frequency selector and phase controller unit 14 for separating the source signal into preselected frequency components having predetermined phase relations, a sonic lens 16 for focusing the output signals from the unit 14 on a target 18, and a laser feedback system 19 for detecting variations in the vibration frequency of the target 18 and using this information to adjust the output signals from the unit 14 to maximize the destructive capability of the system 10.

The power output of the source 12 must be sufficient to destroy the target 18. In addition, the sound pressure level of the source signal must be adequate to render the signal transmission medium nonlinear, since, as is discussed above, medium nonlinearity must exist for parametric pumping to take place. As will be apparent hereinafter, it is not absolutely necessary to rely solely on the intensity of the source signal to render the medium nonlinear. However, when the intensity of the signal form the sonic source 12 is relied on, it is estimated that for the frequency band of interest in an air medium, the nonlinear effect becomes significant at sound pressure levels of about 140 db. Since the intensity from the sonic source 12 required to destroy structural targets will generally be greater than 140 db, typically 160-190 db, a source 12 capable of destroying such targets will also be sufficient to render the air medium nonlinear. Various commercially available apparatus, such as rocket and nuclear engines, satisfy these criteria.

Before the design and construction of an appropriate frequency selector and phase controller 14 and sonic lens 16 may be implemented, it is necessary to know the approximate fundamental or base frequency, the approximate frequency of the highest frequency pump signal, the desired effective range of the sonic blast, the desired effective target area of the sonic blast on impact, the diameter of the sonic lens and, finally, the characteristics of the medium.

As is noted above, the destructive capability of the sonic weapon system 10 is maximized when energy transfer from the sonic blast to the target 18 takes place at the resonant frequency of the target. Since the resonant frequency of most structures is typically 5-20 hertz, a base or fundamental frequency of 5 hertz is desirable. Assuming the preferred air medium, a maximum pump signal frequency of about 5,000 hertz is presently preferred since at higher frequencies attenuation losses are so great that the contribution from any such signal would be insignificant. For weapons applications, a 50 feet diameter zone of focus at the point of impact is presently preferred. Referring to Rayleigh's equation above, and recognizing that $\sin \phi \approx$ lens diameter/range for the ranges of interest, it is apparent that the diameter of the sonic lens 16 is directly dependent on the desired range of the weapon. When the desired portability of the system 10 is taken into account, a lens diameter of 50 feet is presently preferred. Solving Rayleigh's equation using these parameters yields an effective range of about 5,000 feet, which is considered strategically acceptable.

Referring now to FIG. 2, the preferred frequency selector and phase controller 14 is shown. As illustrated, the unit 14 preferably comprises a plurality of tubular elements 30, here shown to be eleven tubular elements 30a–30k, each having a mask 32 and a fan 34 at one end 35 thereof, the masks and fans being unnumbered in the tubes 30h–30k for purposes of clarity. The speed of the fans 34 is variably controlled by a fan speed controller 40 and, for reasons that will be more fully apparent hereinafter, the masks 32 are preferably fixed relative to the tubes 30.

To accommodate the output of the sonic source 12, it is presently contemplated that each of the tubular elements 30 will have a diameter of approximately 10 feet. Since the diameter at the output of an engine of the types contemplated for use as the source 12 is approximately 10 feet, the unmasked or input ends 36 of the tubular members 30 are preferably connected to the sonic source 12 by a frustoconical connecting member 38 which has its narrow end joined to the output of the sonic source 12 and its widened end joined to the input ends 36 of the tubular members 30.

As discussed above, in order for the sonic weapon system 10 to be effective, the unit 14 must be capable of separating the raw output from the sonic source 12 into discrete frequency components comprising the fundamental frequency (5 hertz), a first pump signal having a frequency twice the base frequency (10 hertz), a second pump signal having a frequency twice that of the first pump signal (20 hertz), and additional pump signals, the frequency of each being twice that of the preceding pump signal, with the final pump signal having a frequency in the desired range, here selected to be about 5,000 hertz. In addition, augmentation of the fundamental frequency will not take place unless each frequency component is 90° out of phase with the next lowest frequency component. In other words, the 10 hertz pump signal must be 90° out of phase with the 5 hertz signal, the 20 hertz pump signal 90° out of phase with the 10 hertz pump signal, and so on. While the unit 14 could be designed to generate discrete frequency components having purely sinusoidal wave forms, this is not necessary. All that is necessary is that the selected wave forms have cyclical maxima which satisfy the specified frequency requirements. For example, sound pulses having a pulse repetition frequency meeting the above requirements would suffice. Accordingly, throughout the specification and claims, the term "frequency" is to be understood as the repetition rate of the selected wave form, whether it be sinusoidal, pulse, triangular, etc. The discrete frequency components at the output of each of the tubes comprising the unit 14 are best characterized as triangular waves. Referring to Table I below, the desired output frequencies of each of the eleven tubes 30a–30k illustrated in FIG. 2 is shown wherein the 5 hertz output signal from the tube 30a represents the fundamental frequency and the 5,120 hertz output signal from the tube 30k represents the highest pump frequency.

TABLE I

| Tube 30 | Speed of Rotation in RPM's | Mask Sections | Output Frequency (hertz) |
|---|---|---|---|
| a | 300 | 1 | 5 |
| b | 600 | 1 | 10 |
| c | 1,200 | 1 | 20 |
| d | 2,400 | 1 | 40 |
| e | 4,800 | 1 | 80 |
| f | 4,800 | 2 | 160 |
| g | 4,800 | 4 | 320 |
| h | 4,800 | 8 | 640 |
| i | 4,800 | 16 | 1,280 |
| j | 4,800 | 32 | 2,560 |
| k | 4,800 | 64 | 5,120 |

Figure 2B:
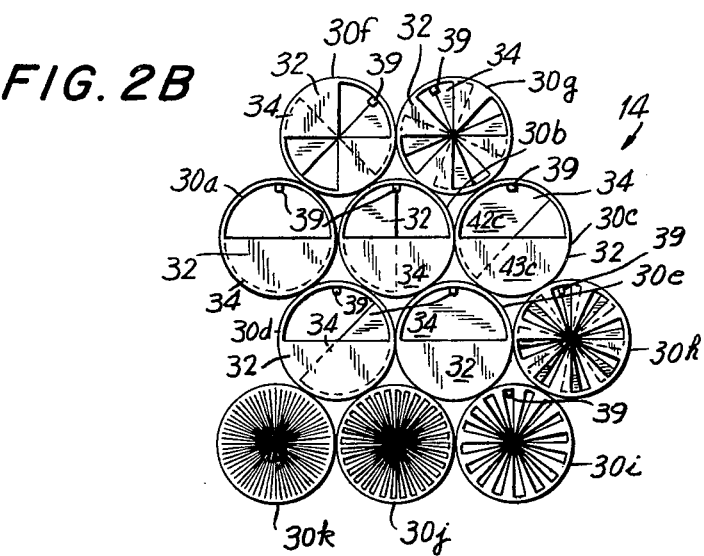
FIG. 2B is a front elevation of the frequency selector and phase controller of FIG. 2A.

As may be best seen in FIG. 2B, the fans 34a–34e disposed in the ends 35 of the tubular elements 30a–30e each consists of a single semicircular blade 42, the diameter of each blade 42 being equal to the internal diameter of its corresponding tube 30. The masks 32 disposed in the ends 35 of the tubes 30a–30e preferably each consist of a single mask section 43 of the same size and shape as the fan blades 42a–42e. For purposes of clarity, only the fan blade 42c and mask section 43c are numbered in FIG. 2.

Figure 3A:
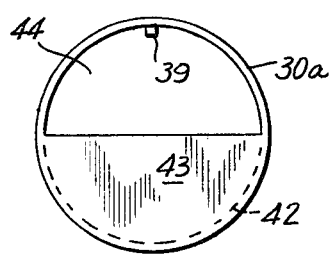
FIG. 3A is a front elevation of the tube 30a in FIG. 2 wherein the fan blade is positioned to pass air.
Figure 3B:
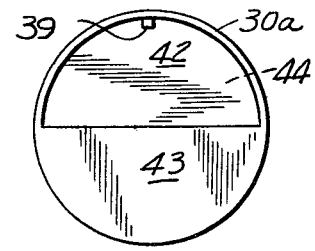
FIG. 3B is a view similar to FIG. 3A except that the fan blade is positioned to block air.

Thus, as the blades 42a–42e rotate, each will pass through a first position in which the blade 42 is fully overlapped by its corresponding mask section 43 (FIG. 3A) and a second position in which there is no overlap between the blade 42 and its mask section 43 (FIG. 3B). It will thus be apparent that in the first position half of the opening 44 is exposed while in the second position the opening 44 is completely blocked. Thus, as air is blown through the tubes 30a–30e by the sonic source 12, the masks 32a–32e and fans 34a–34e cooperate to alternately pass and block the exit of air through the openings 44 thus forming air pulses at the output of these tubes. Clearly, the frequency of these pulses depends on the speed of rotation of the fans 34 which, as already noted, is regulated by the fan speed controller 40. Thus, if the fan 34a is rotated at 300 rpm, the frequency of the air pulses emanating from the end 35 of the tube 30a will be 5 hertz. Likewise, if the fan 34b is rotated at 600 rpm, the frequency of the air pulses emanating from the tube 30b will be 10 hertz. It will likewise be apparent that by successively doubling the speed of rotation of the fans 34c–34e up to a maximum speed of 4,800 rpm, the frequency of the air pulses emanating from the tubes 30c–30e will be 20 hertz, 40 hertz, and 80 hertz, respectively. (See Table I.)

Because of anticipated design problems, it is not presently desirable to rotate any of the fans 34 at speeds above 4,800 rpm and, therefore, frequencies above 80 hertz cannot be generated by using semicircular masks and fans with increased fan speeds. In accordance with the present invention, this problem is preferably overcome by maintaining the speed of rotation of the fans 34 in the tubes 30f–30k at 4,800 rpm while doubling the number of fan blades 42 and mask sections 43 in each successive tube. For example, referring again to FIG. 2B, it may be seen that the fan 34f is comprised of two fan blades 42f, each blade comprising a quarter circle having a radius equal to the internal radius of the tube 30f. Likewise, the mask 32f is also comprised of two quarter-circle sections 43f each having a radius equal to the internal radius of the tube 30f. It will thus be apparent that during each rotation of the fan 34f, the baldes 42f will twice assume positions in which the mask sections 43f completely overlap the blades and twice assume positions in which no portion of the mask sections 43f overlap the fan blades 42f. Consequently, two air pulses will emanate from the tube 30f for each full rotation of the fan 34f. If, as is presently preferred, the speed of rotation of the fan blade 34f is 4,800 rpm, it will be apparent that the frequency of the pulses emanating from that tube will be 160 hertz (see Table I). By successively doubling the number of fan blades 42 and mask sections 43 in each of the remaining tubes 30g–30k while maintaining the fan speed at 4,800 rpm, the frequency of the pulses emanating from these tubes will be 320 hertz, 640 hertz, 1,280 hertz, 2,560 hertz, 5,120 hertz, respectively (see Table I).

As noted above, rotation of the fans 34 is effected by the fan speed controller 40. Controller 40 is, in turn, driven by an appropriate prime mover, the sonic source 12 being presently preferred. The rotational speed at the output of the controller 40 is preferably selected as 4,800 rpm to match the highest required fan speed, with rotation of the individual fans 34 preferably being accomplished through suitable gearing arrangements. Since the design and construction of a suitable fan speed controller 40 and suitable gearing arrangements are well within the capabilities of the skilled art worker, further descriptions thereof are deemed unnecessary and none are given. When fan speed control is effected on this basis, it will be apparent that the frequency of the output signals emanating from the unit 14 may be accurately controlled by varying the primary rotational speed of the fan speed controller 40 and that the required frequency ratios between the fundamental and pump signals will be maintained as the speed of the controller 40 is varied.

It is presently preferred that rotation be imparted to the fans 34 at their peripheries since the conventional approach of rotating the fans at their centers is complicated by the magnitude of the pressures involved. For example, the fan blades 42 of the fans 34 could be secured at their peripheries to the internal annular surface of an external annular gear supported for rotation in its corresponding tube by suitable bearings. As shown in FIG. 2A, the masks 32 are preferably secured to the tubes 30 on the outward facing side of the fan 34 although they could, if desired, be disposed on the inward facing side as well.

While phase control can be introduced into the system 10 in a variety of ways, the preferred approach is to include a differential in the gearing for each tube fan 34. Then, if a particular fan requires phase advance or retardation, the differential gearing for that fan may be adjusted as desired. Since the design and construction details of such differentials are well known to those skilled in the art, a further description thereof is deemed unnecessary and none is given.

To maintain the required 90° phase separation between the different frequency components generated by the unit 14, pressure sensors 39 (FIG. 2) are preferably disposed at the ends 35 of each of the tubes 30 such that the pressure changes resulting from the alternate blockage and passage of air through the tubes 30 may be sensed. (For purposes of clarity, the sensors 39 are not shown in tubes 30j and 30k). The time differential between pressure peaks for the different frequency components may then be compared to determine whether the desired 90° phase relation is present. The differential gearings to the fans 34 may be adjusted to correct any errors.

The unit 14 may also include means for regulating the levels of the signals emanating therefrom. This can be accomplished, for exanple, by introducing diaphragms at the inlet ends 36 of the tubes 30 following the example of diaphragms used in cameras to control the diameter of the lens opening.

Figure 4:
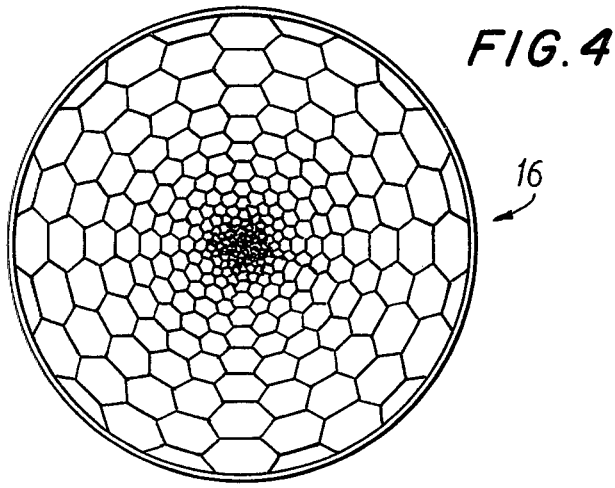
FIG. 4 is a front elevation of the preferred sonic lens.

Referring now to FIG. 4, the preferred sonic lens 16 for focusing the signals emanating from the tubes 30 on the target 18 is shown. To be effective, the sonic lens 16 must be capable of focusing each of the different frequency components emanating from the unit 14. In addition, the lens 16 will preferably also be capable of effecting fine control of the phasing amongst the reflected components.

As shown in FIG. 4, the preferred sonic lens 16 comprises a concave honeycomb array. It may be seen in FIG. 5 that each unit of the array comprises a preferably hexagonal tubular structure 60 closed at one end 62. Preferably, the cross-sectional area of the tubes and the tube lengths are adjusted to provide tuning of the discrete frequency components incident thereon, a preferably equal number of individual honeycombs 60 being tuned to each frequency.

Figure 5:
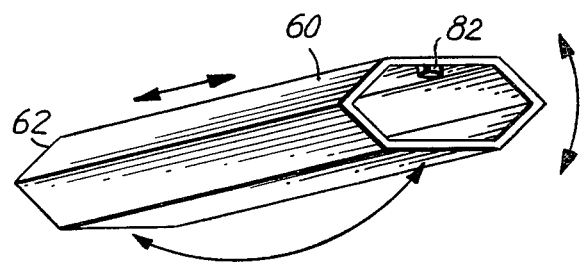
FIG. 5 is a perspective view of one of the honeycomb units which make up the lens of FIG. 4, the arrows indicating axes of motion.

As shown by the arrows in FIG. 5, each honeycomb unit 60 is preferably supported for horizontal rotation (pan adjustment), vertical rotation (tilt adjustment) and front to back linear motion (depth adjustment). Pan and tilt adjustment of the individual honeycombs 60 gives the lens 16 the capability for individually focusing each honeycomb on the target 18. A pan adjustment of ±30° and tilt adjustment of ±20° should be sufficient for this purpose. The depth adjustment permits fine phase adjustment of the discrete frequency components generated by the unit 14 by allowing the starting point of the nonlinear interaction between these components to be varied. The phase adjustment introduced by the front to back linear motion of the individual honeycomb units is, of course, in addition to the phase differential introduced by the differential gearing arrangements discussed above in connection with the unit 14. Since it is contemplated that the depth adjustment of the individual honeycomb units will be used to effect fine phase adjustments only, and considering the relatively long wavelengths of the focused signals and the short travel distance between the unit 14 and the lens 16, a front to back linear travel of ±2 feet should be sufficient.

The phasing of the various frequency components reflected from the lens 16 may be checked by using pressure sensors 82 (FIG. 5) similar to the pressure sensors 39 on the unit 14 (FIG. 2). As shown in FIG. 5 the sensors 82 are preferably disposed at the open ends of each of the honeycomb units 60. Again, these sensors serve to check phasing by measuring the time differential between pressure peaks for the different frequency components, any necessary adjustments being made by adjusting the relative depths of the tubes 60 in the array as is more fully discussed above.

Suitable arrangements for effecting pan, tilt and depth adjustments are well known to those skilled in the art and such arrangements may be used herein. For example, commercial grade movie cameras have this capability. On this basis, a further description of the means for adjusting the orientation of the individual honeycomb units 60 is deemed unnecessary. Suffice it to say that all connections will preferably be made to the backs 62 of the individual units 60, the backs being selected solely on the basis of accessibility.

The sonic source 12, frequency selector and phase controller 14 and sonic lens 16 may, by themselves, be effectively used as a sonic weapon and these three components comprise the basic embodiment of the present invention. However, as noted above, energy transfer from the system 10 to the target 18 is maximized when the fundamental frequency of the sonic blast is matched to the resonant frequency of the target 18. Moreover, it must be recognized that as fissures, cracks, etc. begin to appear, the resonant frequency of the target may change. Therefore, and as shown in FIG. 1, the preferred sonic weapon system 10 includes a laser feedback system 19 for continuously sensing the resonant frequency of the target 18. The output signal from the system 19 is then used to adjust the fan speed controller 40 to match the fundamental frequency of the unit 14 to the resonant frequency of the target 18.

As diagrammatically illustrated in FIG. 1, the preferred laser feedback system 19 includes a laser 20, an interferometer 22, a frequency analyzer 24 and a band pass filter 26. The output from the laser 20 is split. The first beam is directed at the target and reflected therefrom to the interferometer 22, while the second beam is introduced directly into the interferometer. As is well known, by employing a photocell or similar device, the interferometer 22 can measure movement of the target 18 based on changes in the light pattern produced when the two laser beams are combined. Laser interferometers having sufficient resolution for incorporation in the sonic weapon system 10 are commercially available. For example, the Model 5526A laser interferometer marketed by Hewlett-Packard is capable of measuring distance with a resolution of one millionth of an inch. Also acceptable is Hewlett-Packard's Model 5501A which can measure distance with a resolution of six-ten-millionths of an inch. Based on preliminary estimates, this is at least a thousand times more accurate than is required for the system 10.

While the range of these instruments, approximately 200 feet, is limited by the range of the lasers incorporated therein, their range can be increased by using a more powerful laser as, for example the Keuffel and Esser Rangemaster. The Rangemaster, which operates on a different principle than the lasers incorporated in the Hewlett-Packard interferometers, has a range of up to about forty miles.

The frequency analyzer 24 is, as shown, connected to the output of the interferometer 22 and serves to determine the frequency of motion of the structure based on variations in the light pattern resulting from interference of the two laser beams. Thus, the output of the frequency analyzer 24 is a signal indicative of the frequency of motion of the target 18. Before applying this signal to the input of the fan speed controller 40, it is desirable to filter the signal to reduce unwanted system noise. As presently preferred and shown, this is accomplished by using the band pass filter 26 which serves to eliminate frequencies outside the range of interest. Since the design and construction of frequency analyzers 24 and band pass filters 26 suitable for incorporation in the system 10 are well known to those skilled in the art, further descriptions thereof are deemed unnecessary.

The frequency of the laser beam directed to the target 18 is preferably chosen for maximum ability to penetrate haze, dust, and other atmospheric disturbances. Based on these consideration, a helium-neon laser, operating in the red portion of the visible spectrum, is presently preferred. To insure the accuracy necessary to obtain a meaningful signal at the output of the frequency analyzer 24, the laser 20 and interferometer 22 should be kept as stationary as possible and isolated from ground vibrations. When designing the optical system, care should be taken to insure that only the light beam reflected from the target 18 can enter the interferometer 22. This latter feature is a characteristic of commercially available laser interferometers such as those discussed hereinabove.

Figure 6:
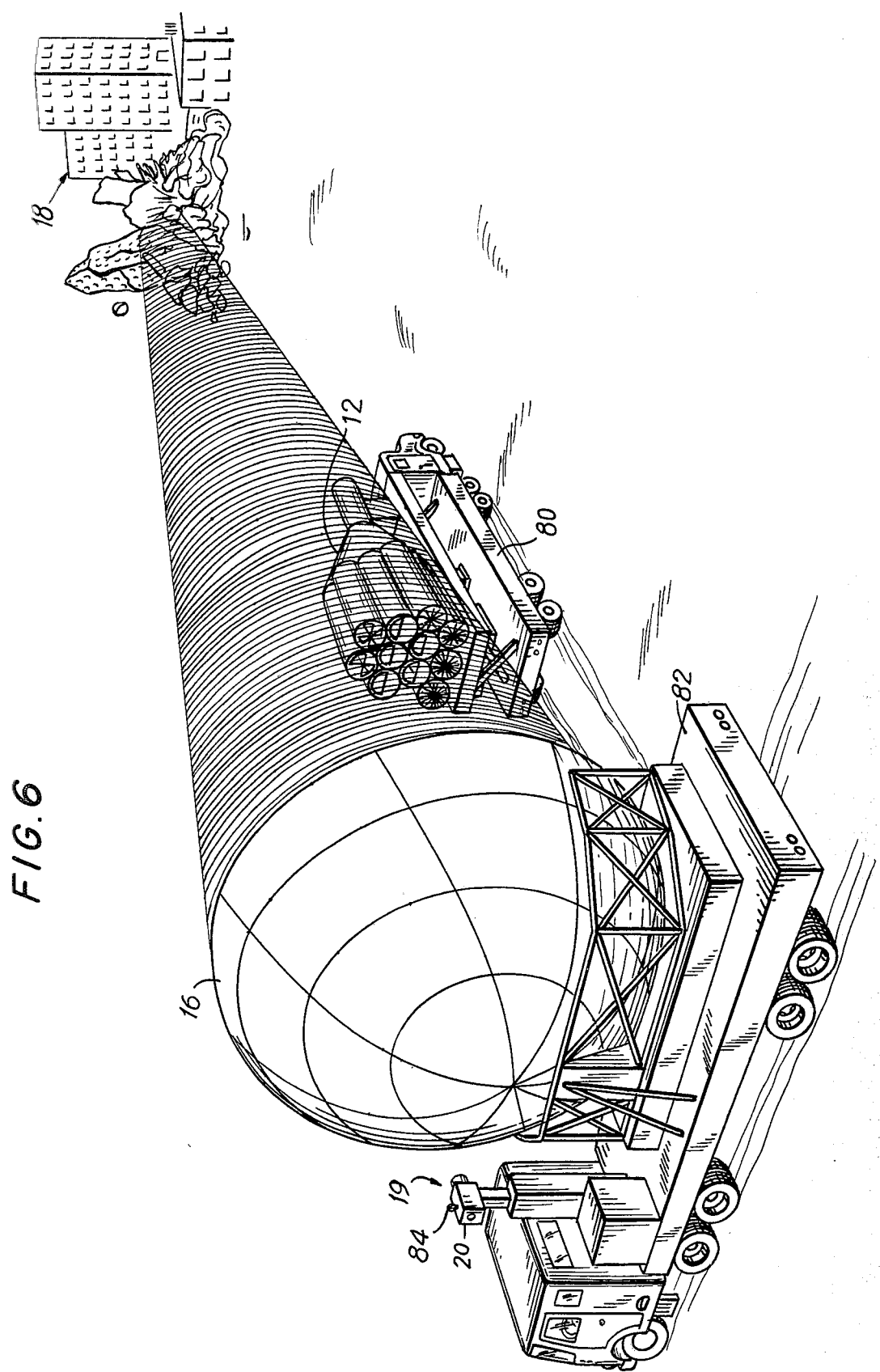
FIG. 6 is a perspective view of the preferred sonic weapon system in operation.

Referring now to FIG. 6, the preferred sonic weapon system 10 together with means for transporting the weapon system to the target site are illustrated. As shown, the sonic source 12 and frequency selector and phase controller 14 are mounted on a first flatbed truck 80. The sonic lens 16 and the laser feedback system 19 are mounted on a second flatbed truck 82. The trucks will be driven to a site within the range of the sonic lens 16 and positioned such that the reflecting surface of the lens is directed at the target 18 and the unit 14 is directed at the lens but offset from the axis thereof. Accordingly, the assembly comprised of the source 12 and the unit 14 is preferably movably mounted on the flatbed truck 80 such that pan and tilt adjustments can be made. Likewise, the sonic lens 16 is also preferably movably mounted on the truck 82 for pan and tilt whereby the orientation of the lens may be adjusted. Since these pan and tilt adjustments may become defocused due to source vibrations during firing, means are preferably provided for monitoring them during firing and readjusting them as necessary.

Operation commences with the operator sighting the target 18 by using a sight 84 on the laser 20 provided for this purpose. The mechanisms for rotating and tilting the sonic lens 16 and for adjusting the relative orientations of the individual honeycomb units 60 thereof will preferably be operatively connected to track the laser 20 whereby sighting the target in the laser will simultaneously focus the lens. At or prior to this point, the laser feedback system 19 and the fan speed controller 40 are activated, the primary rotational speed of the controller 40 being initially selected to match the estimated resonant frequency of the target 18. Firing is commenced by activating the source 12.

As firing continues, the laser feedback system 19 senses variations in the resonant frequency of the target 18 and readjusts the speed of the controller 40 to vary the fundamental frequency of the unit 14 as required.

Preferably, the outputs from the pressure sensors 39 and 82 are also continuously monitored to insure that the desired 90° phase differential between successive frequency components prevails, the necessary adjustments being made on a continuous basis during firing.

It will be apparent from the foregoing that effective operation of the sonic weapon system 10 requires the continuous readjustment of a number of parameters. This, combined with the desirability of rapid readjustment for maximizing the destructive capability, dictates that the number of manual operations be minimized. Accordingly, it is presently preferred that the sonic weapon system 10 be computer controlled.

As diagrammatically illustrated in FIG. 7, the computer 90 receives signals from the laser tracking mechanism, the laser feedback system 19, and the pressure sensors 39 and 82, and processes this information to provide output signals indicative of the adjustments required. After suitable conditioning, these output signals are used to adjust the physical orientation of the unit 14 relative to the sonic lens 16; adjust the pan and tilt of the individual honeycomb units 60 for optimum focus; adjust the fan speed controller 40 to keep the system fundamental frequency in step with the resonant frequency of the target 18; and adjust the differential gearings to the individual tube fans 34 and the depth of the units 60 to maintain 90° phasing. As shown in FIG. 7, the computer 90 is also preferably connected to one or more output devices, such as the CRT 92, for accommodating monitoring of system operation. The computer controller is also preferably connected to an input device, such as the terminal 94, for feeding basic information, such as the target range and expected target resonant frequency into the computer, and for accommodating overrides when necessary. Since the design, implementation and programming of a suitable computer system for carrying out these functions is well within the capabilities of the skilled art worker once the method and parameters of the operation of the system 10 are known, further descriptions thereof are deemed unnecessary.

While computer control is preferred, the system 10 could be operated without the computer by having the operator monitor the signals which would otherwise be inputted to the computer and manually effect adjustment either directly or through appropriate mechanical-electronic/electrical controls. Most preferably, the system 10 will be provided with the capability for both computer and manual control to accommodate operation when the computer is down.

Preliminary calculations have been carried out based on the sonic weapon system 10 to assess its efficacy. These calculations assumed a power transmission efficiency of 30% based on expected losses from atmospheric attentuation, beam spreading, loss of energy to harmonics, etc. It was also assumed that the target structure consisted of a building 50×50×100 feet high with four concrete walls one foot thick. For a resonant frequency of approximately 5 hertz, these calculations indicate that it will take approximately 13.2 seconds to destroy the entire structure, that approximately 11 gallons of jet fuel will be consumed, and that the required sound level at the target will be approximately 169 db. Similar calculations were carried out for a building 50×50×100 feet high with walls two feet thick. Assuming a resonant frequency of 10 hertz, these calculations indicate that the entire structure could be destroyed in about 6.2 seconds, that approximately 84 gallons of jet fuel will be consumed and that the sound pressure level at the target must be about 181 db.

In addition to destroying structures, the weapon system 10 could be effectively utilized to selectively disable or kill enemy troops depending upon the sound level selected. Since troop disablement requires less power and higher frequencies, a system limited to this application could use a smaller lens and a less powerful sonic source. Apart from wartime applications, it will be apparent that the system 10 has peace time uses as well, building demolition being one example. If used for this purpose, the sonic source need not be as powerful as the source 12 required for the system 10 since the required transmission range is not as great.

Figure 8:
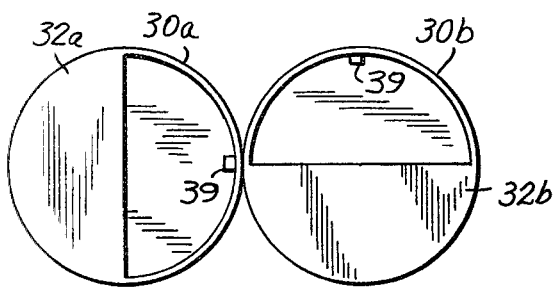
FIG. 8 is a front elevation of the tubes 30a and 30b in FIG. 2B showing an alternative means for effecting phase control.

Once the preferred sonic weapon system 10 described hereinabove is known, those skilled in the art will appreciate that various additions and modifications may be made thereto without departing from the spirit and scope of this invention. For example, while phase control of the unit 14 is preferably accomplished by employing differential gearing, this is not absolutely necessary. For example, phasing can be effected by adjusting the relative orientations of the masks 32 at the ends 35 of the tubes 30. Thus, as shown in FIG. 8 for the case of the tubes 30a and 30b, by rotating the mask 32b one quarter turn relative to the mask 32a, it will be apparent that the signal exiting the tube 32a will lead the signal exiting the tube 32b by 90°. It will be further apparent that by rotating each successive mask 32c–32k one quarter turn relative to the preceding one, each frequency component exiting the unit 14 will lag the next lower one by 90° and the desired phasing will have been achieved.

Figure 9:
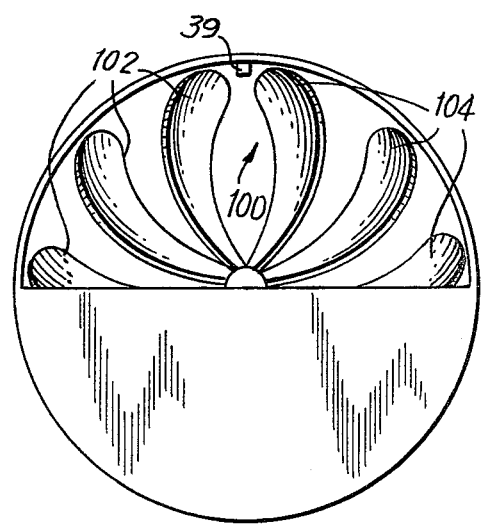
FIG. 9 is a front elevation of one of the tubes shown in FIG. 2B illustrating an alternative means for generating high level, discrete frequency sound waves.

In a further modification of the unit 14, the conventional fans 34 illustrated in FIG. 2 are replaced with fans having blades which push air in both directions. When this embodiment is used, a separate sound source such as the sonic source 12 would not be used and fan blades 42 would themselves generate sound. For example, as shown in FIG. 9, the fan 100 could be substituted for the fans 34 used to generate the five low frequency components in FIG. 2. As shown, half of the fan 100 has blades 102 oriented for pushing air in one direction while the other half 104 are oriented for pushing air in the reverse direction. It will be apparent from FIG. 9 that the fan blades 102 and 104 contribute to the air flow as they come out from behind the mask 32. For example, if all the blades which push air forward are exposed at one time there would be a maximum forward thrust of air. As the fan rotated, there would be a combination of both forward and reverse blades exposed which would slow the forward thrust. At a still later point, only those blades which were pushing air in the reverse direction would be exposed. The principal advantage of this approach is that the resulting sound pressure waves will be approximately triangular in shape and thus will more closely approximate sinusoidal air flow. When this modification is employed, energy input could be derived, for example, from the source utilized as the sound source 12 in the FIG. 1 embodiment, the only difference being that the source now serves to rotate the fan blades. The arrangement illustrated in FIG. 9 may be utilized to generate the higher frequency components by adding additional opposed blade sections, the number of opposed blade sections required being equal to the number of mask sections required in the FIG. 2 embodiment as set forth in Table I. Phasing of a plurality of fans 100 could be introduced by differential gearing, relative rotation of the masks, or any other suitable techniques.

The FIG. 9 embodiment may be further modified by providing fan blades and masks at both ends of the tube. This arrangement would be more truly resonant than those discussed above with the length and cross-section of the tube and the phasing of the fan blades and masks providing highly selective sound filtering and sound generation capabilities.

As noted above, it is not necessary to rely solely on the intensity of the sound generated by the sonic source 12 to render the transmission medium, typically air, nonlinear. Thus, for example, the transmission medium may be rendered nonlinear or its nonlinearity enhanced by periodically introducing shock waves along the transmission path. Such shock waves, which are familiar when a body passes through air at supersonic speeds or highly compressed air is suddenly released, result in a rapid rise in pressure that is propagated through the medium. It is presently contemplated that such shock waves will be used to enhance the nonlinearity of the air medium by introducing them into the transmission path in synchronization with the fundamental frequency of the system 10. Since, as is discussed above, the conversion efficiency obtainable by nonlinear parametric pumping is dependent on medium nonlinearity, enhancing the nonlinearity of the medium will increase the overall efficiency of the system 10.

Still further changes and modifications may be made. For example, while the tubes 60 which make up the lens 16 have been described as having preferably hexagonal cross-sections, this is not necessary and other cross-sectional configurations, such as circular cross-sections, may be substituted. In any event, because of the high sonic levels and numerous moving parts, aerospace design techniques will preferably be employed throughout.

Since these as well as further changes and modifications may be made within the scope of the present invention, the above description should be construed as illustrative and not in a limiting sense, the scope of the invention being defined by the following claims.

I claim:

1. A system for transmitting a parametrically pumped sonic signal through a transmission medium to a remote location comprising:
    a sound source
    means for separating the sound from said source into a plurality of discrete frequency components including a fundamental component and at least one additional component, each additional component having a frequency twice that of the next lowest frequency component;
    means for adjusting the phase difference between each frequency component and the next lowest frequency component to substantially 90°;
    means for colinearly focusing said components on said remote location; and
    means for rendering said transmission medium nonlinear between said focusing means and said remote location.

2. The system of claim 1, wherein said signal separating means comprises:
    a plurality of frequency selective elements, each comprising:
        (a) a tubular structure defining a longitudinal passage communicating with an inlet end and an outlet end;
        (b) means disposed in said tubular structure for obstructing a portion of said passage; and
        (c) means movably disposed in said tubular structure for alternately exposing and blocking the remainder of said passage; and
    means for controlling the time lapse between exposures of said remainders of said passages.

3. The system of claim 1, wherein said means for rendering said medium nonlinear comprises said sound source.

4. The system of claim 1, wherein said means for rendering said medium nonlinear comprises means for generating shock waves and introducing said shock waves into said transmission medium at said fundamental frequency.

5. The system of claim 1,
    wherein said remote location comprises an object; and
    further comprising:
        (a) means for sensing the vibration frequency of said object and for generating an output signal indicative thereof; and
        (b) means responsive to said output signal for adjusting the frequency of said fundamental frequency component to match the vibration frequency of said object and for adjusting the frequencies of said additional frequency components for maintaining each additional component at twice the frequency of the next lowest frequency component.

6. The system of claim 1, and
    further comprising means for sensing the phase difference between said frequency components and for generating an output signal indicative thereof; and
    wherein said phase difference adjusting means is responsive to said output signal.

7. The system of claim 2, wherein said obstructing means comprises a mask and said movable means comprises a fan.

8. The system of claim 2, wherein:
    said sound source comprises an engine; and
    each of said inlet ends is oriented to receive a portion of the sound from said engine and said output ends are oriented to direct sound entering said inlet ends to said focusing means.

9. The system of claim 1, wherein said focusing means comprises a plurality of tubular structures each defining a longitudinal passage having a closed end and an open end, said open ends being oriented to receive the sound output from said separating means.

10. The system of claim 2, and further comprising means for regulating said controlling means for varying the frequency of said fundamental frequency component and for adjusting the frequencies of said additional frequency components for maintaining each additional component at twice the frequency of the next lowest frequency component.

11. The system of claim 2, and
    further comprising means for sensing the phase difference between said frequency components and for generating an output signal indicative thereof; and
    wherein said adjustment means are responsive to said output signal.

12. The system of claim 3, wherein said means for rendering said medium nonlinear further comprises means for generating shock waves and introducing said shock waves into said transmission medium at said fundamental frequency.

13. The system of claim 5, wherein said vibration frequency sensing means comprises a laser interferometer.

14. The system of claim 7, wherein said controlling means comprises means for rotating said fans at different speeds.

15. The system of claim 7, wherein said controlling means comprises:
  means for rotating said fans; and
  each of said masks and said fans having different numbers of sections and blades, respectively.

16. The system of claim 7, wherein:
  said sound source comprises said fans; and
  each fan comprises a segment including a blade for pushing air towards said outlet opening and a blade for pushing air away from said outlet opening.

17. The system of claim 7, wherein said phase difference adjustment means comprises each mask being rotated an amount equal to a 90° phase difference relative to the mask in the tubular structure corresponding to the next lowest frequency component.

18. The system of claim 9, wherein said focusing means further comprises means for adjusting the pan and tilt of each of said tubular structures.

19. The system of claim 9, wherein said phase difference adjusting means includes means for adjusting the depth of each tubular structure relative to the depth of the other tubular structures.

20. The system of claim 9, wherein the dimensions of said passages are preselected to enhance the reflection of said frequency components.

21. The system of claim 10,
  wherein said remote location comprises an object;
  further comprising means for sensing the vibration frequency of said object and for generating an output signal indicative thereof; and
  wherein said regulating means is responsive to said output signal for matching said fundamental frequency to said vibration frequency.

22. The system of claim 11, wherein said sensing means comprises pressure transducers disposed at the output ends of said tubular structures.

23. The system of claim 14, wherein said controlling means further comprises the mask and fan in at least one of said tubular structures having a different number of sections and blades, respectively, than the mask and fan in at least one other tubular structure.

24. The system of claim 14, wherein said fan speed controlling means comprises a rotating member and gearing means connected to said rotating member and said fans for rotating said fans upon rotation of said rotating member.

25. The system of claim 15, wherein the number of mask sections in each tubular structure is equal to the number of fan blades in that tubular structure.

26. The system of claim 16, wherein said controlling means comprises means for rotating said fans at different speeds.

27. The system of claim 16, wherein said controlling means comprises:
  said fans having different numbers of segments; and
  means for rotating said fans.

28. The system of claim 16, wherein said masks and fans are disposed at the outlet ends of their respective tubular structures.

29. The system of claim 19, and
  further comprising means for sensing the phase difference between said frequency components at the open ends of said tubular structures and for generating an output signal indicative thereof; and
  wherein said depth adjusting means is responsive to said output signal.

30. The system of claim 20, wherein a plurality of tubular structures enhance the reflection of each frequency component.

31. The system of claim 23, wherein the number of mask sections in each tubular structure is equal to the number of fan blades in that tubular structure.

32. The system of claim 24, wherein said phase difference adjustment means comprises a differential in said gearing means for each fan.

33. The system of claim 26, wherein said controlling means further comprises at least one of said fans having a different number of segments than at least one other fan.

34. The system of claim 28, and further comprising additional masks and fans disposed at the inlet ends of said tubular structures.

35. The system of claim 29, wherein said sensing means comprises pressure transducers disposed in the output ends of said tubular structures.

36. The system of claim 1, further comprising means for regulating the amplitude of said components.

* * * * *